United States Patent [19]
Ito et al.

[11] Patent Number: 5,643,322
[45] Date of Patent: Jul. 1, 1997

[54] METHOD AND APPARATUS TO REDUCE SKIN TISSUE BY USING HIGH-VOLTAGE PULSES

[75] Inventors: Yoshihiro Ito, Kyoto; Kazushi Miyake, Tokyo, both of Japan

[73] Assignee: Institute of General Beauty & Medical Science, Tokyo, Japan

[21] Appl. No.: 406,522

[22] Filed: Mar. 20, 1995

Related U.S. Application Data

[63] Continuation-in-part of Ser. No. 151,857, Nov. 15, 1993, abandoned.

[30] Foreign Application Priority Data

Jan. 26, 1993 [JP] Japan .................................. 5-29818

[51] Int. Cl.$^6$ ...................................... A61N 1/40
[52] U.S. Cl. .............................................. 607/2
[58] Field of Search .......................... 604/20; 607/1, 607/2, 50, 63, 65–67, 70–72, 75, 94, 100, 115, 145, 150, 154

[56] References Cited

U.S. PATENT DOCUMENTS

| | | | |
|---|---|---|---|
| 1,337,894 | 4/1920 | Forshee | 607/154 |
| 1,463,392 | 7/1923 | Hanson et al. | 607/154 |
| 2,073,428 | 3/1937 | Schmid | 607/72 |
| 3,881,494 | 5/1975 | Paul, Jr. | 607/72 |
| 4,093,975 | 6/1978 | Roberts | 607/72 |

*Primary Examiner*—William E. Kamm
*Attorney, Agent, or Firm*—Richard Linn

[57] ABSTRACT

The present method is a method for reducing an oxidized skin tissue comprising the steps of bringing a source of negative high-voltage pulses of which duty ratio is controllable into the proximity of the oxidized skin tissue and applying negative high-voltage pulses to the oxidized skin tissue so that the oxidized skin tissue is reduced by an electron addition reaction. A high-voltage generating circuit which is incorporated in a main body generates negative high-voltage pulses. Those negative high-voltage pulses are applied to the skin through a contact element which is connected to the main body, so that the oxidized skin tissue is reduced by the electron addition reaction. Further, the present apparatus is an apparatus to reduce a skin tissue, comprising a high-voltage pulse generating means to generate negative high-voltage pulses, and a contact element which is connected to the high-voltage pulse generating means and applies negative high-voltage pulses generated by the high-voltage pulse generating means to the skin when it is brought close to or in contact with a surface of the skin, whereby an oxidized skin tissue is reduced by the electron addition reaction.

15 Claims, 12 Drawing Sheets

COUPLING CONSTANT OF Mn(II): $g_0 = 2.0042$
FREQUENCY OF Mn(II)
RESONATING MAGNETIC FIELD: $A_0 = 9.39 mT$

FIG. IIA
START
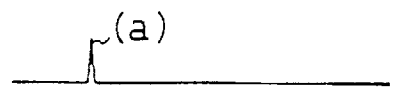
(a)
FIG. IIB
1HR
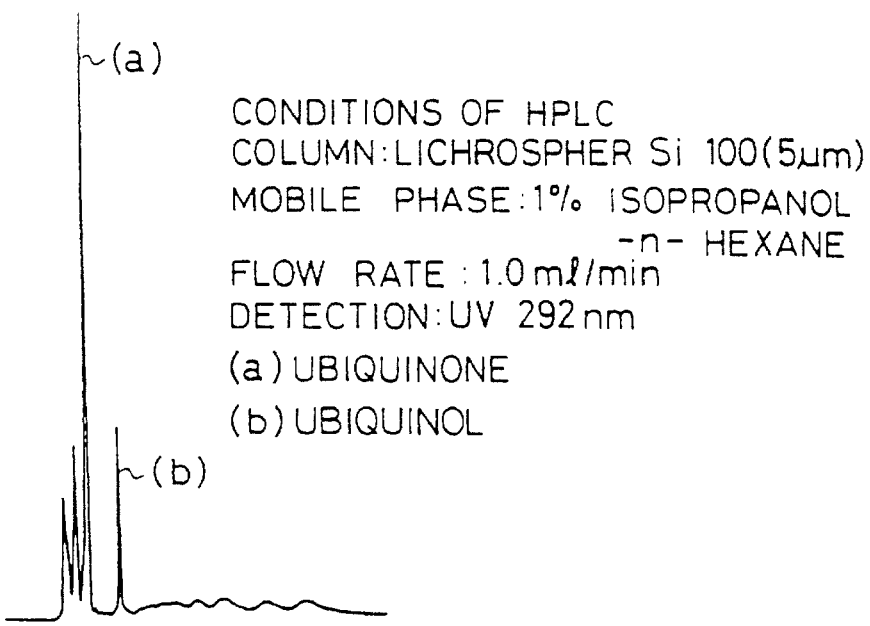
CONDITIONS OF HPLC
COLUMN: LICHROSPHER Si 100(5μm)
MOBILE PHASE: 1% ISOPROPANOL
            -n- HEXANE
FLOW RATE: 1.0 mℓ/min
DETECTION: UV 292nm
(a) UBIQUINONE
(b) UBIQUINOL
FIG. IIC
2HR
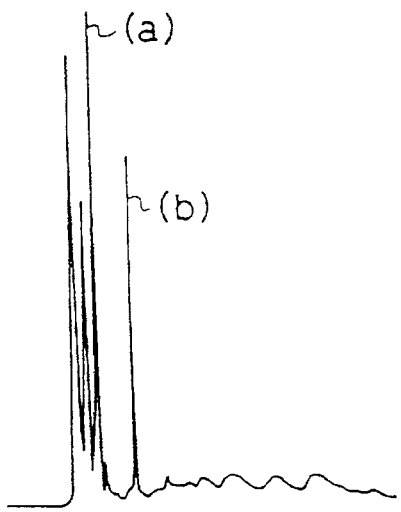
FIG. IID
3HR
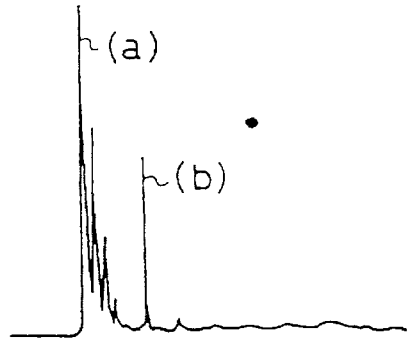

START

2HR

CONDITIONS OF HPLC
COLUMN: LICHROSPHER Si 100(5μm)
MOBILE PHASE: 1% ISOPROPANOL
    -n- HEXANE
FLOW RATE: 1.0 ml/min
DETECTION: UV 292nm

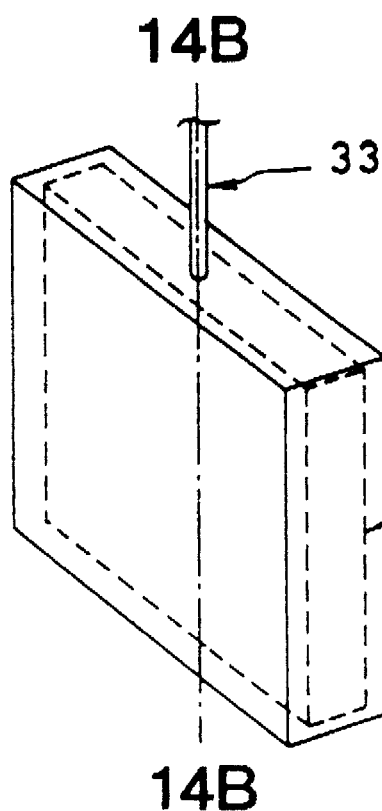
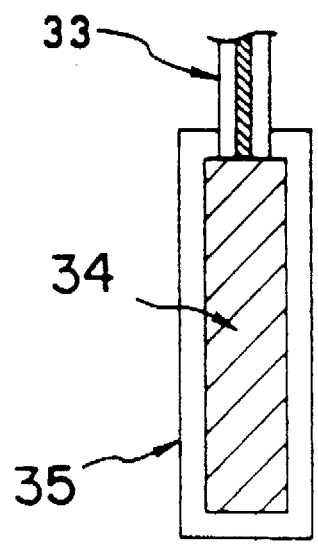
FIG. 14A          FIG. 14B

METHOD AND APPARATUS TO REDUCE SKIN TISSUE BY USING HIGH-VOLTAGE PULSES

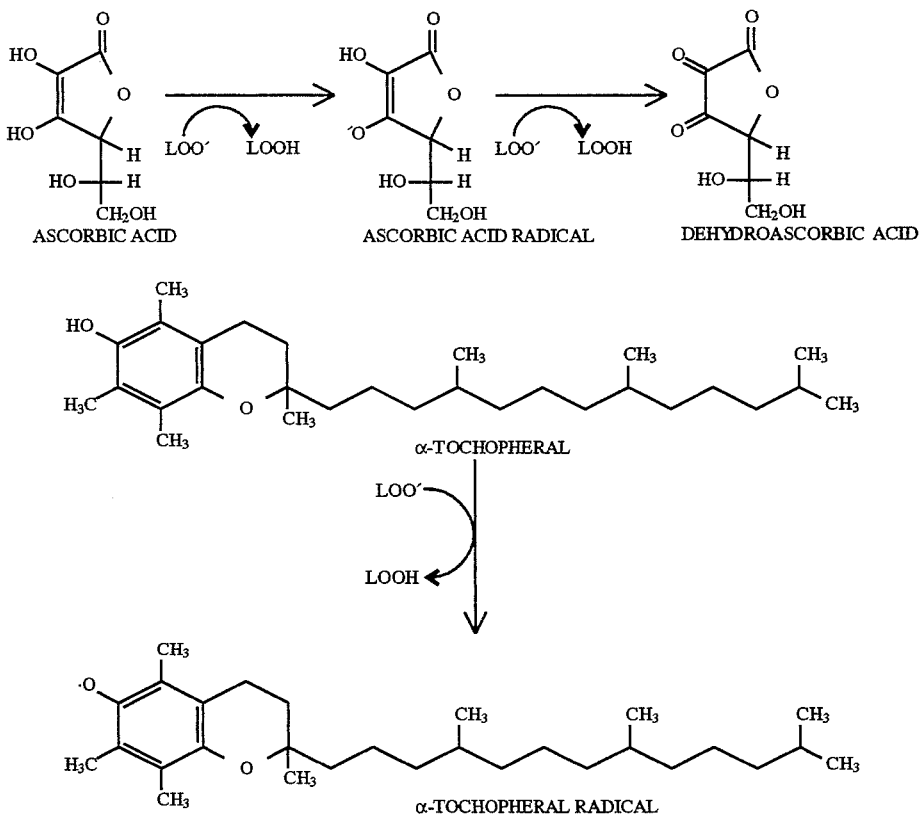

Chemical Reaction Formula 1

CROSS-REFERENCE TO RELATED APPLICATION

This application is a continuation-in-part of our prior application Ser. No. 151,857, filed on Nov. 15, 1993, entitled "METHOD AND APPARATUS TO REDUCE SKIN TISSUE" and now abandoned.

BACKGROUND OF THE INVENTION

1. Field of the Invention

The present invention relates to a method and apparatus to reduce oxidized skin tissue of a live body such as a person, and more specifically, to the method and apparatus to electrically or electronically reduce the oxidized skin tissue by using high-voltage pulses of which duty ratio and voltage are respectively controllable. The reduction is achieved through addition of electrons caused by the high-voltage pulses.

2. Description of the Related Art

One of the factors that causes deterioration of the skin of a live body is oxidation of the skin tissue. When the skin tissue is oxidized, its metabolic function is damaged and the activation of the skin tissue is prevented. Accordingly, in order to prevent the deterioration of the skin of the live body, the oxidized skin tissue would be reduced. One of the methods to reduce the oxidized skin tissue that has been conventionally employed is ingestion of tocopherol (vitamin E) or ascorbic acid (vitamin C) yielding in vivo reducing function as shown in a below chemical reaction formula 1.

In the above mentioned method for reducing the oxidized skin tissue, reducing substances such as the vitamin C must be ingested, and since those reducing substances cannot be synthesized in vivo, they must be ingested through foods or drugs in a form of synthesized products. However, the vitamin C ingested in a form of the foods or synthesized products takes a lot of time to be brought to the oxidized skin tissue to reduce it. In addition, since the vitamin C ingested spreads all over the body, the vitamin C does not contribute only to the reduction of the oxidized skin tissue, but rather the reduction effect may be dispersed through the whole body, which may lead to unexpectedly low results.

SUMMARY OF THE INVENTION

In view of the above-described problems of the known prior art, the present invention is aimed at providing a method and an apparatus for steadily and effectively reducing oxidized skin tissue in a short time period.

According to one aspect of the present invention, for achieving the objects described above, there is provided a method to reduce oxidized skin tissue comprising the steps of bringing a source of negative high-voltage pulses of which duty ratio is controllable into the proximity of the oxidized skin tissue and applying negative high-voltage pulses to the oxidized skin tissue, so that the oxidized skin tissue is reduced by an electron addition reaction.

According to another aspect of the present invention, there is provided an apparatus to reduce an oxidized skin tissue, comprising a high-voltage pulse generating means to generate negative high-voltage pulses, and a contact element, which is connected to the high-voltage generating means and which applies negative high-voltage pulses generated by the high-voltage generating means to the skin when it is brought close to or in contact with the surface of the skin, so that the oxidized skin tissue is reduced by an electron addition reaction.

The nature, principle and utility of the invention will become more apparent from the following detailed description when read in conjunction with the accompanying drawings and diagrams.

BRIEF DESCRIPTION OF THE DRAWINGS

In the accompanying drawings:

FIGS. 11A to 11D are graphs showing an HPLC of ubiquinone in E$_t$OH-H$_2$O(3:1) solutions before and after irradiation of the skin tissue reducing apparatus according to the present invention;

FIG. 14A is perspective view showing another example of the contact element used in the skin tissue reducing apparatus;

FIG. 14B is a cross-sectional view for a B—B line in FIG. 14A;

DESCRIPTION OF THE PREFERRED EMBODIMENT

Generally speaking, when an atom, a molecule or an ion acquires electrons, it is called "reduced". That means, the reduction is a reaction due to an addition of electrons having negative electric charges. For example, an iron ion of tri-valent $Fe^{3+}$ is reduced to an iron ion of di-valent $Fe^{2+}$ by adding an electron $e^-$ as shown in the below chemical reaction formula 2. A manganese ion of hepta-valent $Mn^{7+}$ is reduced to a manganese ion of di-valent $Mn^{2+}$ by the addition of five electrons (5e') as shown in the below chemical reaction formula 3.

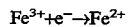

Chemical Reaction Formula 2

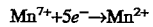

Chemical Reaction Formula 3

Accordingly, it is possible to electrically reduce the oxidized skin tissue of a live body.

In fact, it is known that the potential energy of an ion in the reduced state is greater than that of the precursor, and there is a great energy barrier between the state transitions. Thus, the in vivo reduction is performed with the intervention of an energy transmission system and an enzyme. Accordingly, a relatively high voltage (or field strength) is required for reducing the oxidized skin tissue electrically or electronically. In order to carry out electrically efficient reduction of the oxidized skin tissue, an AC or a pulsed voltage is required, which can easily penetrate the skin.

From the above description, it can be concluded that an efficient electrical reduction of the oxidized skin tissue requires an application of negative high-voltage pulses controlled the duty cycle and/or voltage to the skin.

Figure 1:
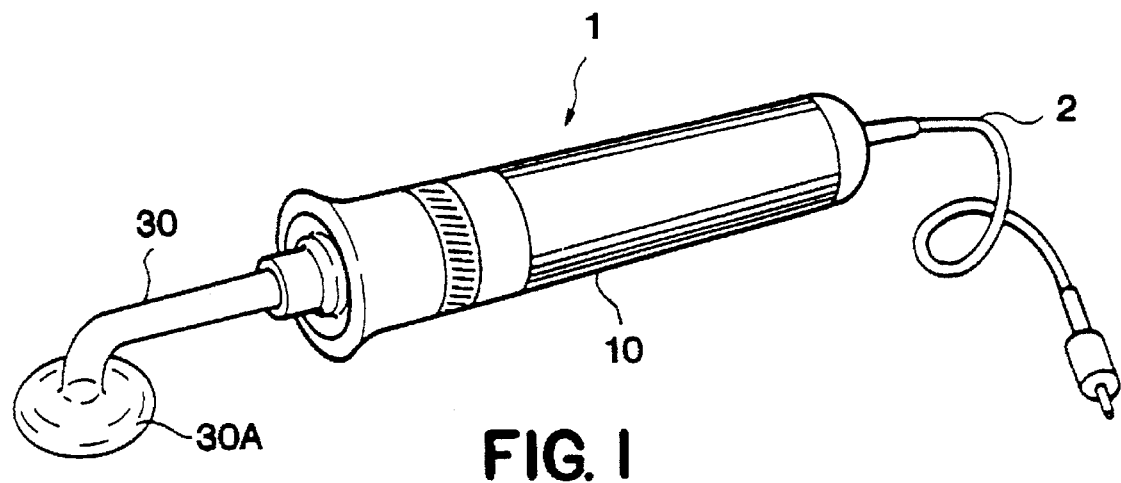
FIG. 1 illustrates a perspective view of one example of a skin tissue reducing apparatus according to the present invention.
Figure 15A:
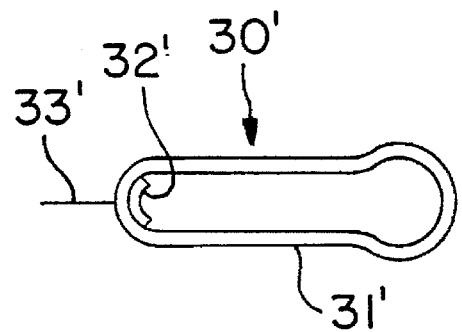
FIGS. 15A and 15B show other examples of glass tube contact elements for use in the skin tissue reducing apparatus.
Figure 15B:
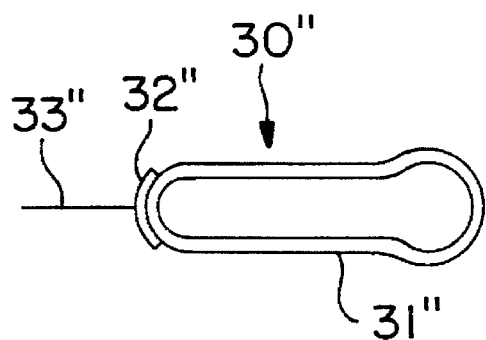

FIG. 1 illustrates a perspective view of one example of a skin tissue reducing apparatus 1 according to the present invention, wherein a main body 10 including an electric circuit (high-voltage pulse generating means) and a contact element 30 are provided, and the main body 10 is a portable cylindrical form and a power source line 2 is connected to one side bottom portion thereof. The contact element 30 functions to guide negative high-voltage pulses generated by a high-voltage pulse generating means to the surface of the skin. When the skin tissue reducing apparatus 1 is brought close to or in contact with the skin surface, a sufficient coupling is formed with the skin. The contact element 30 which attached to the main body 10, incorporates the high-voltage pulse generating means within the main body 10 and is mounted on another side bottom portion thereof. An end terminal of the power source line 2 is connected to a DC power source or an AC power source to operate the skin tissue reducing apparatus 1. The contact element 30 has a contact portion 30A in a form of an umbrella at the top portion thereof so as to contact with the skin. Besides, the contact element 30 is attachable and detachable to the main body 10. Another function of the contact element 30, in addition to the above-mentioned one, is to give appropriately dispersed impedance to prevent the skin from being burnt by the concentration of the electric current. The contact element 30 which has the above functions and is used in the present invention includes the following forms:

① a glass tube with an electrode coated on one end, in which air or gas having a reduced pressure is sealed (see FIG. 15B, element 30").

Figure 2:
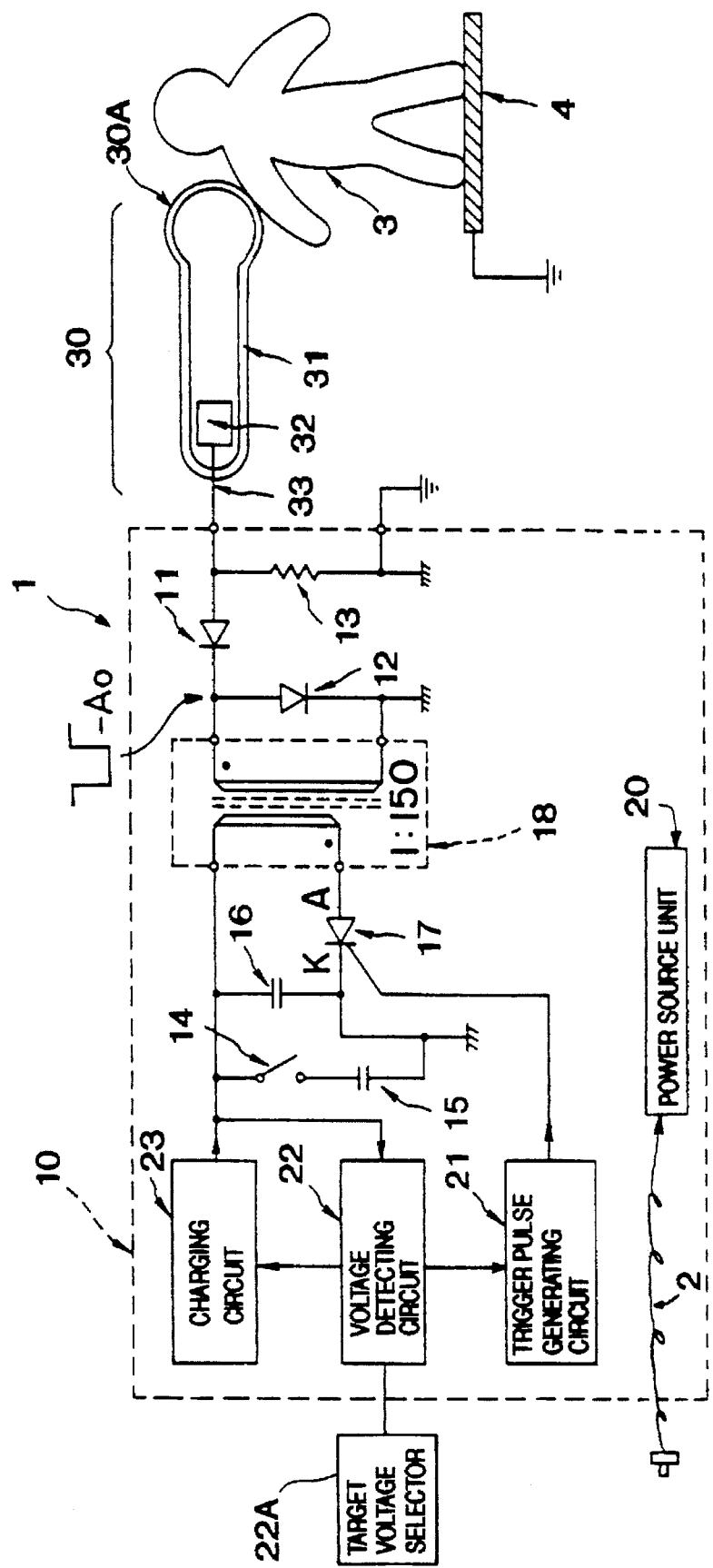
FIG. 2 is a block diagram showing the structure of one example of a high-voltage generating means incorporated in the skin tissue reducing apparatus according to the present invention and a person to be reduced.

② a glass tube in which air or gas having a reduced pressure, and an electrode are sealed (see FIG. 2, element 30).

③ a glass tube in which air or gas having a reduced pressure is sealed and a metal deposition electrode is formed on an inner wall of the glass tube (see FIG. 15A, element 30').

Figure 14C:
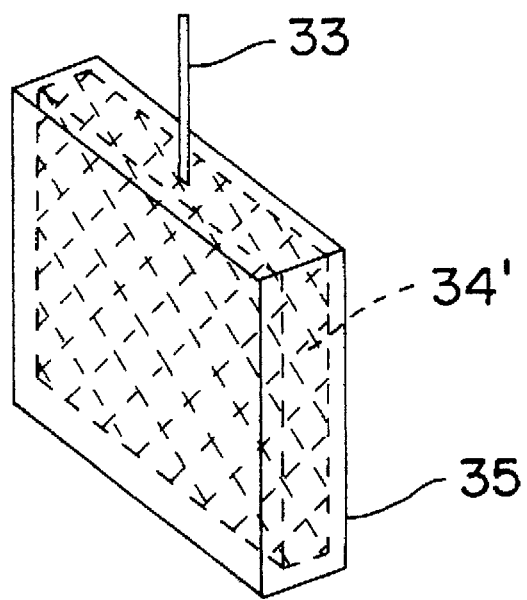
FIGS. 14C and 14D are perspective views showing other examples of contact elements coated with insulating material for use in the skin tissue reducing apparatus.
Figure 14D:
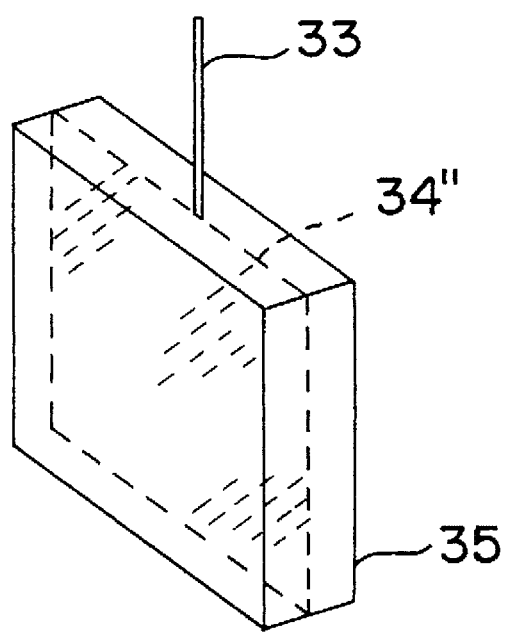

④ a metal plate (FIGS. 14A and 14B, element 34), foil (FIG. 14D, element 34") or net (FIG. 14C, element 34') coated with an insulating material 35 such as glass, resin or the like.

FIG. 2 shows a block diagram illustrating the electrical structure of an example of the skin tissue reducing apparatus 1. The DC voltage (for example, +12 V), which is inputted from a power source unit 20 through the power source line 2 connected to a DC power source or an AC power source, is applied to a trigger pulse generating circuit 21, a voltage detecting circuit 22 and a charging circuit 23. The charging circuit 23 steps up the voltage due to the inputted DC voltage (+12 V) and then quickly charges a main capacitor 16 to an intermediate voltage (e.g., +100 V) to be a target. The voltage detecting circuit 22 always detects the voltage of the main capacitor 16, and the operation of the charging circuit 23 is suspended when the voltage detecting circuit 22 detects the target voltage at the main capacitor 16. An auxiliary capacitor 15 is in parallel connected to the main capacitor 16 through a switch 14. A trigger pulse is applied to a thyristor 17 when the charging to the main capacitor 16 is completed. Then, a path from an anode A to a cathode K of the thyristor 17 is rapidly conducted and a great discharged current from the main capacitor 16 flows to the thyristor 17 through a primary side of a voltage step-up (for example, 1:150) transformer 18.

At this time, high voltage pulses are outputted from a secondary side of the voltage step-up transformer 18 according to its turn ratio. Since the turn ratio is 1:150 and the turn polarity is opposite each other in this embodiment, pulses of −15 kV are outputted at the secondary side to a primary voltage of +100 V. The outputted pulses from the voltage step-up transformer 18 are led to a bleeder resistor 13 and the contact element 30 through a high voltage diode 11.

On the other hand, the discharging current of the main capacitor 16 continues with an attenuation according to a counter electromotive force due to an inductance of the voltage step-up transformer 18 even if the voltage of the main capacitor 16 becomes to zero. The voltage of the main capacitor 16 is finally below a peculiar current value to the thyristor 17 and then the discharging current is stopped by that the thyristor 17 being transferred to OFF-state. At this time, a positive kick-back voltage is occurred at the secondary side of the step-up transformer 18 due to the suspension of the current of the primary side. However, the kick-back voltage is blocked by the high voltage diode 11 and is not led to the contact element 30. As shown in FIG. 2, a fly-wheel diode 12 connected between the thyristor 17 and the voltage step-up transformer 18 can also quickly control the kick-back voltage. When the discharge of the main capacitor 16 is completed, the charging circuit 23 again operates according to a command from the voltage detecting circuit 22 and then the main capacitor 16 is charged for next pulse generation. The above operations are repeated.

In the skin tissue reducing apparatus 1, a value of a negative pulse −A0 outputted from the voltage step-up transformer 18 varies in accordance with the charged voltage of the main capacitor 16 if the turn ratio of the transformer 18 is constant. Therefore, it is possible to adjust the voltage of the negative pulse −A by changing the set voltage of the voltage detecting circuit 22 through a target voltage selector 22 A connected to and forming part of the voltage detecting circuit 22. Since a width τ1 of the negative pulse −A0 is determined according to the capacitance of the main capacitor 16 and the inductance of the voltage step-up transformer 18, it is possible to widen the width τ1 by charging the auxiliary capacitor 15 with the switch 14. A repetition cycle τ1+τ2 of the negative pulse −A0 is independently controllable from the other parameters by adjusting the cycle of the trigger pulse generating circuit 21.

According to the skin tissue reducing apparatus 1, the negative pulses −A0, the pulse width; 5 μs(τ1), the peak value; −15 kV, the repetition cycle; 10 ms, the duty ratio; 1/1999, are outputted from the voltage step-up transformer 18. The contact element 30 is a discharge tube 31 made of thin glass, wherein a nickel electrode 32 is provided and is connected to the high voltage diode 11 and the bleeder resistor 13 through a lead wire 33. Nitrogen gas is sealed in the discharge tube 31 at about 4.5 mmHg pressure. The contact portion 30A of the contact element 30 is contacted to the tissue of a person 3 to be reduced and the person 3 is grounded to the earth through a conductive plate 4. Since there is actually a great capacitance between a surface of the person 3 and the ground, the conductive plate 4 may be omitted.

The operation of the above skin tissue reducing apparatus 1 will be explained hereinafter with reference to the drawings.

When the contact portion 30A of the contact element 30 is contacted on the surface of the person 3, a circuit for generating the negative pulses −A0 in the main body 10 is driven through the trigger pulse generating circuit 21, the voltage detecting circuit 22 and the charging circuit 23 and the discharge is started to output the negative pulses −A0. When the negative pulses −A0 are applied to the nickel electrode 32 in the discharge tube 31 through the high voltage diode 11 and the lead wire 33, glow discharge occurs in the discharge tube 31 and the gas (nitrogen) therein becomes to conductive gas having pertinent impedance and voltage loss. In case of that: a contact opposite area between the discharge tube 31 and the person 3 is 5 cm2, the thickness of the glass of the discharge tube 31 is 0.2 mm, a specific inductive capacity εr of the glass is 7.5 and conductivities of gas in the discharge tube 31 and the person 3 are respectively high, a capacitance Cc is formed at the contact portion as below expression (1):

$$Cc = \epsilon 0 \times \epsilon r \times (5 \times 10^{-4})/(2 \times 10^{-4}) = 166 \text{ pF} \tag{1}$$

If a basic frequency of the pulses outputted from the circuit of the main body 10 is 100 kHz, the impedance Zc having the capacitance Cc is led as the below expression (2) and the pulse current flows.

$$|Zc| = 1/(2\pi fC) = 9.59 \text{ K}\Omega \tag{2}$$

Figure 3:
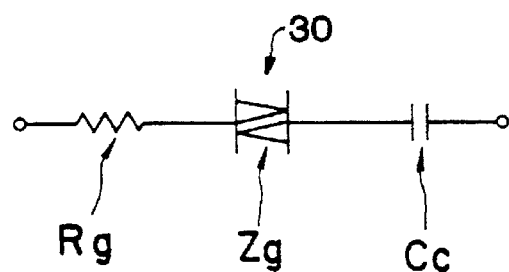
FIG. 3 shows an equivalent circuit of the contact element of the glass tube type.

The discharge tube 31 could be substituted for an equivalent circuit as shown in FIG. 3, wherein a resistor Rg indicates a conductive impedance of the gas, "Zg" indicates a voltage loss with gas discharge and corresponds to a SIDAC (Silicon Diode for Alternating Current) in this example, and the capacitor Cc indicates a capacitance formed through the glass between the gas and the person 3.

Here, in addition to the method using the voltage step-up transformer 18 shown in the above-mentioned embodiment of FIG. 2, a means to generate the negative high-voltage pulses −A0 includes the following methods ① to ③;

① Flyback Method:
An electric current flows to an inductor and a transformer is then shut off quickly.

② Rectification Method:
An AC pulsed high voltage obtained by using a transformer and the like is rectified by a high-voltage rectifier.

Figure 16:
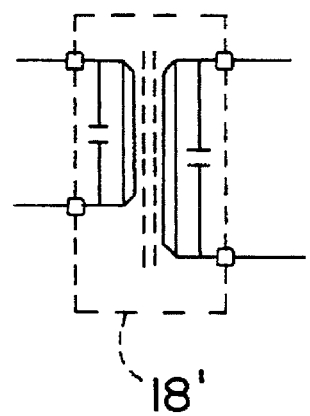
FIG. 16 shows a voltage step-up transformer having resonance type primary and secondary inductance coils.

③ Induction Coil Method:
An electromagnetically inductive coil of resonance type (FIG. 16, element 18') or non-resonance type (FIG. 2, element 18) is employed.

Figure 4:
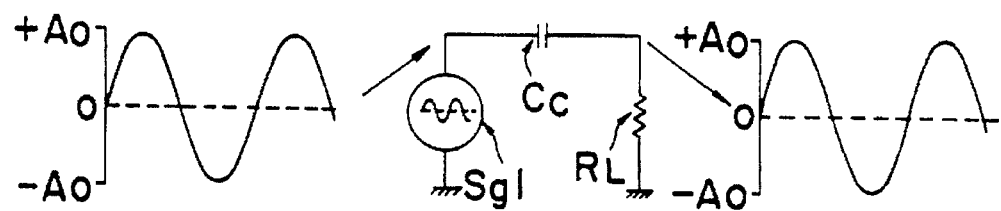
FIG. 4 is a diagram to explain the transmission of a sine wave due to capacitance connection.

In a case of capacitive coupling as shown in FIG. 3, a DC component is not tranaffed. In FIG. 4, a signal source $S_g1$ is a signal source to generate a sine wave of an amplitude $A_o$ and its output impedance is fully low. A resistor RL connected to the capacitor $C_c$ is a load resistance corresponding to the person 3. If a time constant $C_c \times RC$ is fully great to the cycle of the signal source $S_g1$, the wave form of the signal source $S_g1$ is almost equal to the wave form of the voltage VL between both ends of the load resistance RL.

Figure 5:
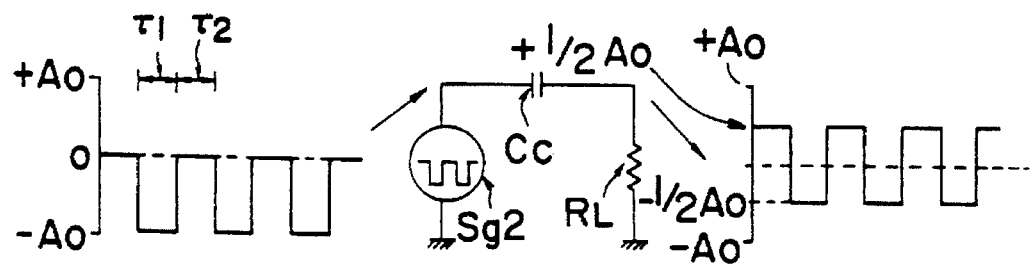
FIG. 5 is a diagram to explain the transmission of pulses of which the duty ratio is 50% due to capacitance connection.

FIG. 5 shows a pulse generating source $S_g2$ which outputs pulses of a pulse height $-A_o$ and a duty ratio $\tau1:\tau2=1:1$ and applies the pulses to the capacitor $C_c$. Since the DC component of the pulses is blocked by the capacitor $C_c$, the voltage VL between the both ends of the load resistor RL becomes to a symmetrical wave for zero volt of an amplitude A0/Z and therefore one polarity is not maintained. Since the electrode side of the load resistor RL for the capacitor Cc is connected with the ground through the load resistor RL, the below expression (3) is established for an integral value of an enough long time and the below expression (4) is established for a positive peak value −Am and a negative peak value Ap for a voltage between the end of the load resistor RL.

$$\int VL \, dt = 0 \quad (3)$$

$$(-Am \times \tau1 + Ap \times \tau2)/(\tau1 + \tau2) = 0 \quad (4)$$

According to the definition of the amplitude, a relationship between the peak values Am and Ap and the amplitude $A_o$ is expressed by the below expression (5) and the expression (6) is established due to that the duty cycle is 1:1.

$$Am + Ap = A_o \quad (5)$$

$$\tau1 = \tau2 \quad (6)$$

The below expression (5) is obtained by substituting the expressions (5) and (6) for the expression(4).

$$Am = Ap = A_o/2 \quad (7)$$

Figure 6:
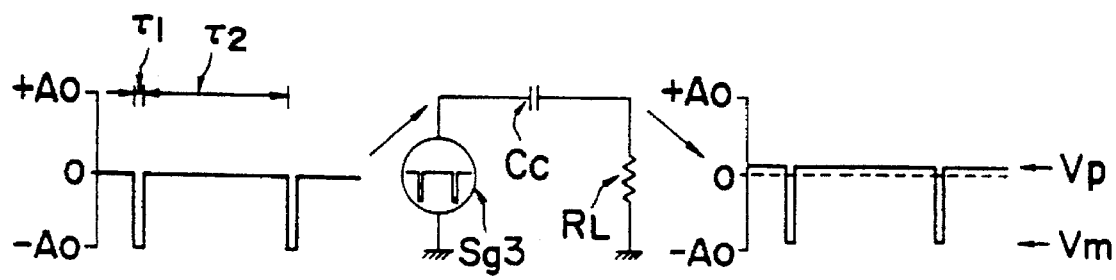
FIG. 6 is a diagram to explain the transmission of pulses of which the ratio is very small due to capacitance connection.

FIG. 6 shows a circuit using a signal source $S_g3$ of which duty cycle $\tau1/\tau2$ is very small. The expressions (4) and (5) are established in this case, and the expression $$Am \times \tau1 = (A_o = Am) \times \tau2 \quad (8)$$

is obtained by modifying the expressions (4) and (5). Therefore, the peak value Am is expressed by the expression (9).

$$Am = \{\tau2/(\tau1 + \tau2)\} \times A_o \quad (9)$$

For example, if the duty cycle $\tau1/\tau2$ is 1/1999, the peak values Am and Ap are obtained as follows:

$$Am = (1999/2000) \times A_o$$

$$AP = A0 - Am = (1/2000) \times A_o$$

According to the above calculations, it is possible to transmit the signal as it almost holds single-pole of the original wave form. If an output peak voltage $A_o$ is 15 KV, a negative voltage Am is 14.9925 KV and a positive voltage Vp is merely 7.5 V. This is a reason that the smallness of the duty cycle is a very important matter in the present invension for holding the single-pole.

As stated above, adjustment and control of parameters of the output wave form are easily performed at the high-voltage pulse generating means in the main body 10. The adjustment parameters are performed by an operating portion (not shown) provided at the high-voltage pulse generating means, or the contact element 30, or an operating portion (not shown) of a remote control means, and the parameters are respectively adjusted to optional values within pespective predetermined ranges in accordance with type and use (e.g., age, physical, constitution, state of skin) of the person 3.

Figure 7:
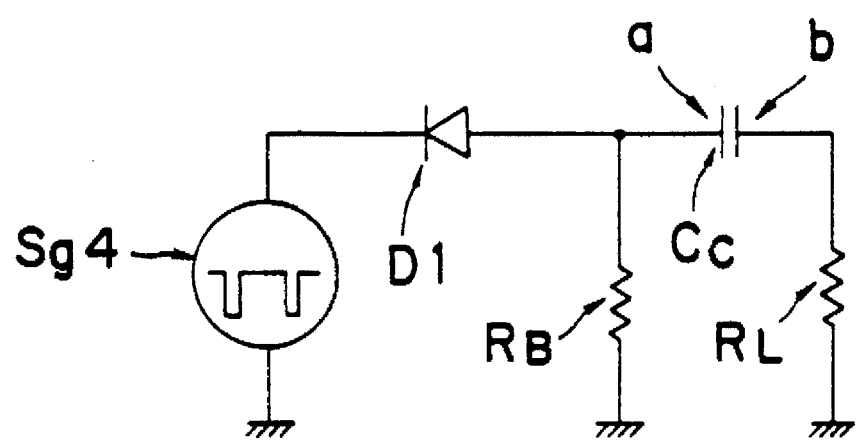
FIG. 7 is an equivalent circuit to explain the necessity of the bleeder resistor.

FIG. 7 shows an equivalent circuit for the bleeder resistor 13 in FIG. 2, wherein a diode D1 is equivalent to the high voltage diode 11 and a resistor RB is equivalant to the bleeder resistor 13. Further, a pulse souce $S_g4$ corresponds to the high-voltage pulse generating means excepted the above elements D1 and 11 and outputs negative pulse of which peak voltage is $A_o$ and impedance is enough low. A capacitor $C_c$ is a coupling capacitance between the contact portion 30A and the shows an impedance for the ground.

In a case of absence of the bleeder resistor RB, it is supposed that electric charge of the coupling capcitor $C_c$ is zero at an initial time. When the negative pulses of the height $-A_o$ are outputted from the pulse source $S_g4$, the high voltage diode D1 is let to "ON". Then, the charging current flows a direction of "GND (ground) →RL→$C_c$→D1→$S_g4$→GND(groound)" and a side "a" of the coupling capacitor Cc is charged negatively and a side "b" thereof is charged positively. Thereafter, when the output of the pulse source $S_g4$ becomes zero, the diode D1 becomes "OFF" and the charging current is blocked. At this time, the side "b" of the coupling capacitor Cc is connected with the ground via the resitor RL and therefore is zero. However, the side "a" of the coupling capacitor Cc is somewhat negative voltage based on the charged electric charges. Since the diode D1 is a state of "OFF", the above electric charges are discharged. The coupling capacitor Cc is gradually charged at each time when the pulses are outputted from the pulse source $S_g4$ so that the voltage of the side "a" approaches to the voltage $-A_o$ and the charging current approaches zero. Finally, the diode D1 always becomes a state of "OFF" and the operation is stopped. This causes serious defects for the skin tissue reducing apparatus 1.

The bleeder resistor RB is connected in order to dissolve above defects. That is, when the pulses are outputted from the pulse source $S_g4$, a current loop of "GND(ground) →RB→D1→$S_g4$→GND(ground)" is formed including the above current loop. However, the current loop does not directly influence to the operation of the present circuit. When the output of the pulse source $S_g4$ transfers to zero, the state of the diode D1 is of course "OFF" and a discharging current flows in a loop of "GND(ground) →RB→$C_c$→RL→GND(ground)" so as to sweep out the electric charges (voltage is Vx) stored at the coupling capacitor $C_c$ during output of the pulses. Although positive voltage corresponding to the discharging current occurs on the load resistor RL during the above operation, the positive voltage does not exceed "Vx×RL/(RB+EL)". Therefore, it is possible to reduce the influence by setting the coupling capacitor $C_c$ greater than a pulse charge at one time, leading the voltage Vx to be small and setting a greater bleeder resistor RB in comparison with the load resistor RL. Since the present invention sets the very small duty ratio for the output pulses, it is possible to insure an enough discharging time in comparison with the pulse output time and to avoid the above defects even if a high resistance is set as the bleeder resistor RB.

Experimental examples to show the reducing effect of the skin tissue reducing apparatus 1 according to the present invention to effectively reduce the skin tissue of the person 3 will be described as follows. The contact element 30 used here comprises a Pyrex thin wall glass tube having a tubular electrode fixed at one end, in which nitrogen of 3 mmHg is sealed.

Figure 8A:
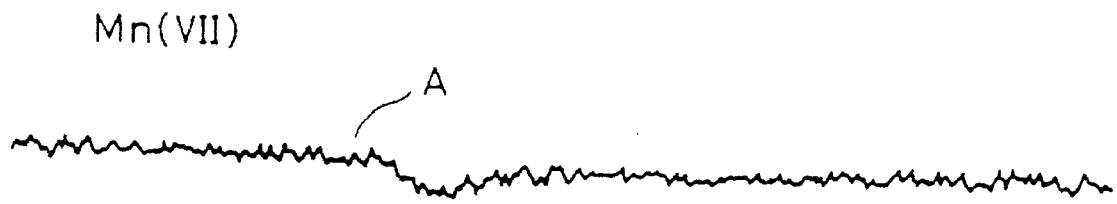
FIG. 8 is a graph showing electron spin resonance (ESR) spectra of A: potassium permanganate solution saturated with pure nitrogen and B: irradiation of the skin tissue reducing apparatus for 45 min. in the solution A.
Figure 8B:
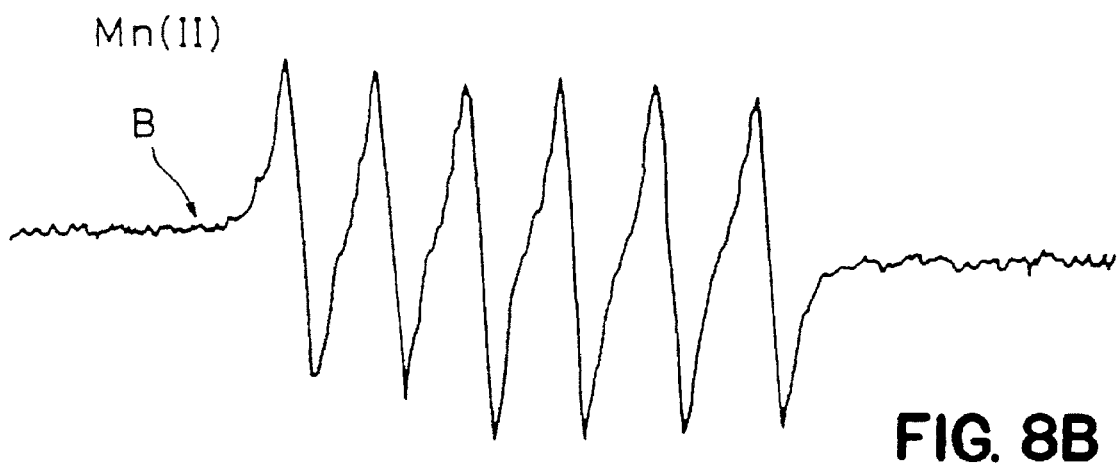

The first experiment was carried out to prove the reduction of Mn (VII) to Mn (II) by addition of electrons using the skin tissue reducing apparatus 1. Irradiation of the skin tissue reducing apparatus 1 to a 0.1 mM potassium permanganate was carried out for 45 minutes. FIG. 8 shows electron spin resonance (ESR) spectra of a curve A before and a curve B after the irradiation of the skin tissue reducing apparatus 1. Since Mn (VII) has diamagnetic characteristics, it does not show the ESR spectrum. After the irradiation, a characteristics A of ESR spectrum of Mn (II) was observed in this solution as shown in a characteristics B of FIG. 8. This result clearly demonstrated that Mn (VII) is changed to Mn (II) by the electon addition effect of the skin tissue reducing apparatus 1 as shown in a below chemical reaction formula 4.

$$Mn^{7+} + 5e^- \rightarrow Mn^{2+}$$

Chemical Reaction Formula 4

As a model, a 0.1 mM potassium permanganate aqueous solution saturated with pure nitrogen was used. FIG. 8 shows characteristic curves on the analytical results of the aqueous solution by an electron spin resonance (ESR) spectra of before and after the contact element 30 of the present apparatus was immersed in the aqueous solution and worked for 45 minutes. As it is clear from the graphs in FIG. 8, the aqueous solution prior to the working of the contact element 30 contained manganese ions Mn (VII) of hepta valent (characteristic curve A), while the aqueous solution after the working, was changed to contain manganese ions Mn (II) of di valent (characteristic curve B). This shows that the manganese ions Mn (VII) was reduced to Mn (II) by the electron addition effect of the skin tissue reducing apparatus 1 according to the present invention.

Figure 9:
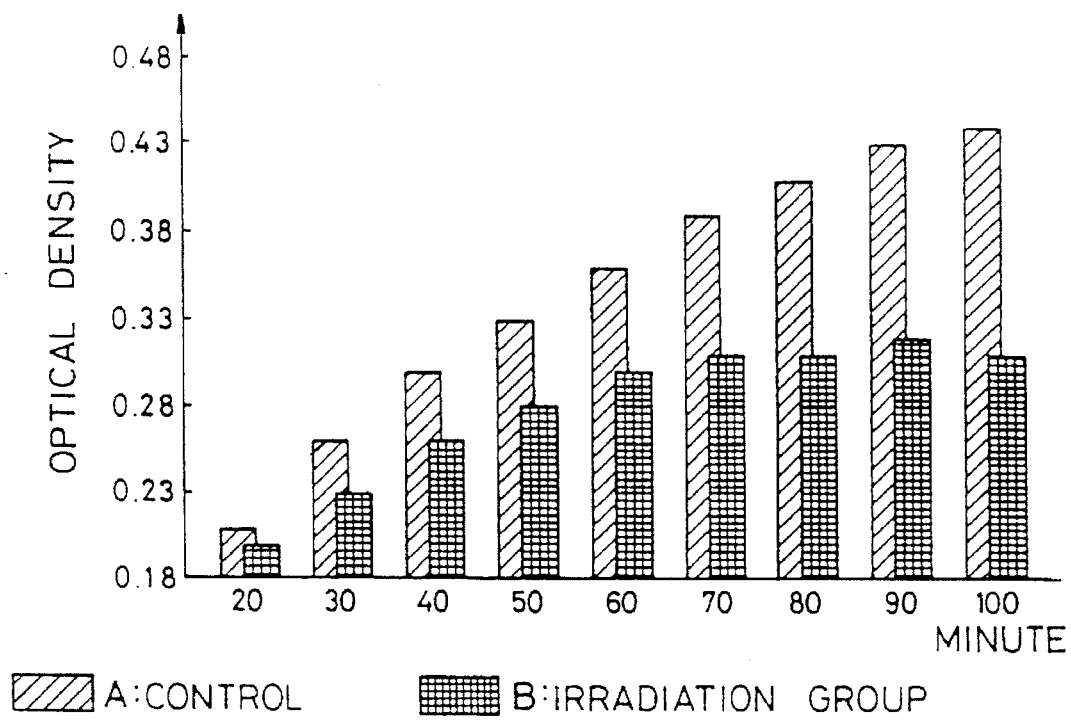
FIG. 9 is a graph showing changes of the optical density at 420 [nm] with time, wherein solution A is pyrogallol solution under atomsphere (control group) and solution B is irradiation of the skin tissue reducing apparatus in the solution A.
Figure 10:
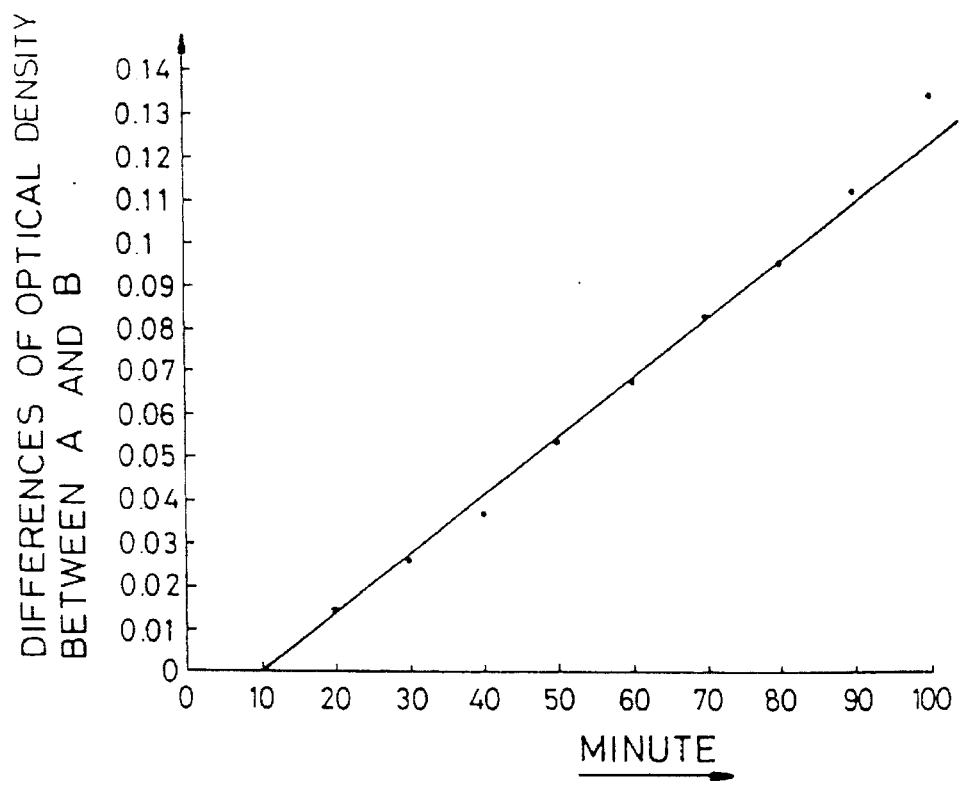
FIG. 10 is a graph showing differences of the optical density at 420 [nm] with time between the solution A (control group) and the solution B (irradiation group) in FIG. 9.

The second experiment was performed based on the reducing effect of an enzyme, superoxide dismutase (SOD) which eliminates peroxides in a living body (refer to a dissertation written by Stefan Marklund and Gudrun Marklund, "Involvement of the Superoxide Anion Radical in the Autoxidation of Pyrogallol and a Convenient Assay for Superoxide Dismutase", Eur. J. Biochem. Vol. 47, 1974, pp.469–474). The pyrogallol solution of the model is a basic solution, subject to autoxidation, colored by the oxidation, and the color is deepened as the degree of the oxidation is raised. Accordingly, when the optical density (O.D.) of the pyrogallol solution is measured by a spectrophotometer as a predetermined wave length, the intensity of the coloration, i.e. the degree of the oxidation can be obtained. The reaction is inhibited by the vitamin C. FIG. 9 shows the change of the optical density at 420 nm with time of A: a pyrogallol solution which was autoxidized under atomosphere (control group), and B: a pyrogallol solution which irradiated by the skin tissue reducing apparatus 1 according to the present invention. As it is clear from the graphs in FIG. 9, it is proved that the oxidation of the pyrogallol solution was inhibited or the oxidized pyrogallol solution was reduced by the skin tissue reducing apparatus 1. FIG. 10 shows the differences of the optical density at 420 nm with time between A (control group) and B (irradiation group). The fact that the difference between the optical density of the pyrogallol solutions is nearly linearly increased with time when the experiments were carried out at a constant voltage and a constant frequency, has demonstrated the reduction effect of the present apparatus.

The third experiment was performed on the reduction of ubiquinone to ubiquinol by using the skin tissue reducing apparatus 1. The ubiquinone and ubiquinol are matter which participate with the transmission of electrons in an organism. It is well known that the ubiquinol strongly have been acting as anti-oxidizing agents in the organism. However, since the ubiquinol are transformed to the ubiquinone by autoxidation and antioxidizing power of the ubiquinol become decreasing. Therefore, it is necessary to give back by reducing the ubiquinone to the ubiquinol.

FIGS. 11A to 11D show a high performance liquid chromatogram (HPLC) of an ubiquinone solution in $EtOH:H_2O$ (3:1), in which the contact element 30 of the present invention was immersed and worked. The analysis result shown in FIG. 11A at start time shows that the initial solution has 100% of the ubiquinone (a). The analysis result shown in FIG. 11B after an hour shows that the solution has 49% of the ubiquinone (a) and 18% of ubiquinol (b). The analysis result shown in FIG. 11C after two hours shows that the solution has 23% of the ubiquinone (a) and 19% of the ubiquinol (b). The analysis result shown in FIG. 11D after three hours shows that the solution has 2% of the ubiquinone (a) and 16% of the ubiquinol (b). These results mean that the ubiquinone is effectively reduced into the ubiquinol by using the skin tissue reducing apparatus 1 as shown in a below chemical reaction formula. 5.

Chemical Reaction Formula 5

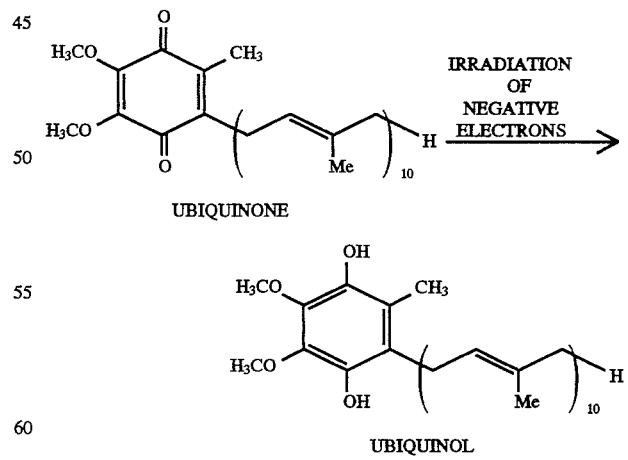

UBIQUINONE

UBIQUINOL

Figure 12:
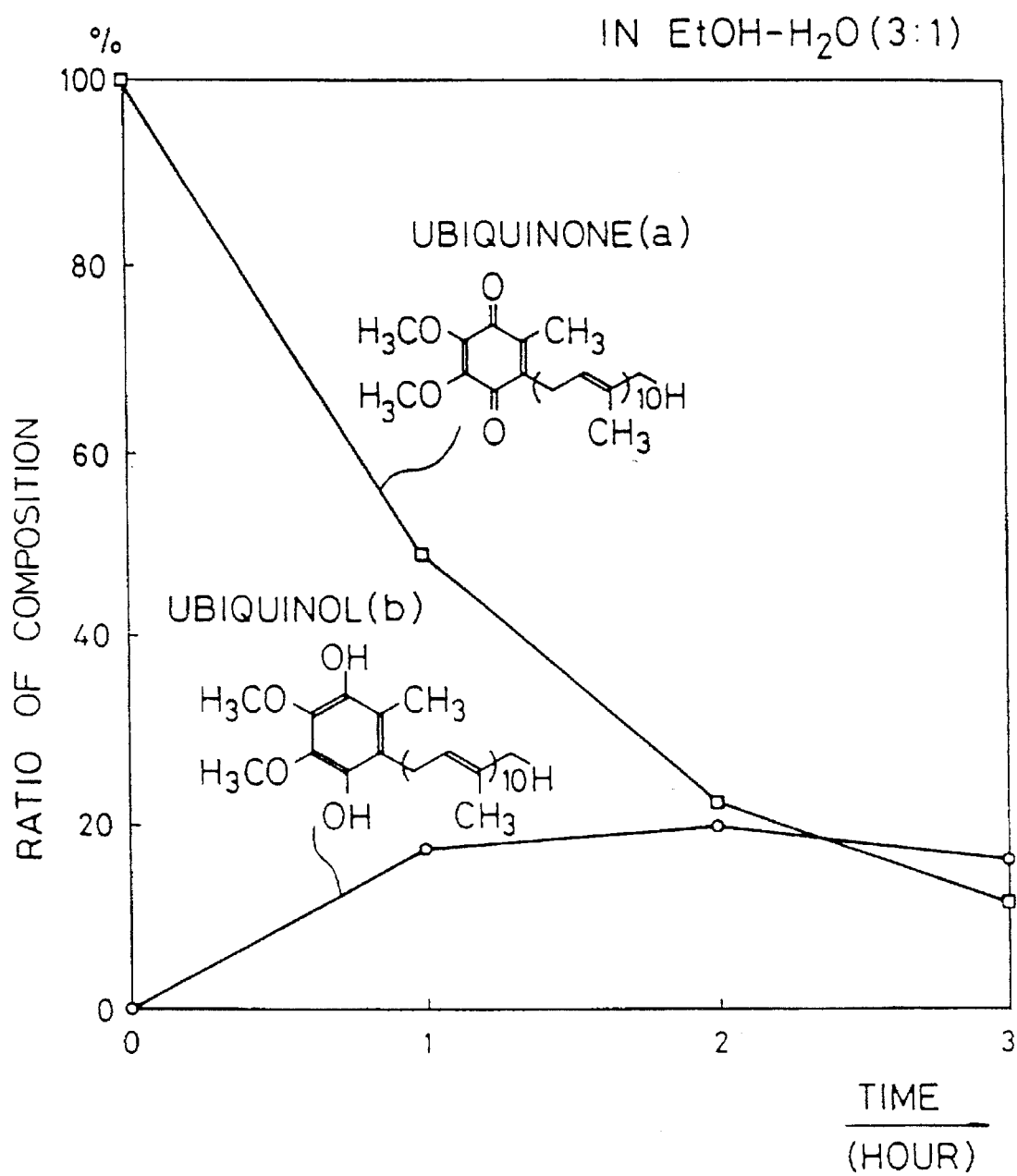
FIG. 12 is a graph showing a ration of the ubiquinone (a) and the ubiquinol (b) by irradiation of the skin tissue reducing apparatus according to the present invention.

Graphs of FIG. 12 show the variation in the difference between quantities of the ubiquinone (a) and the ubiquinol (b) shown in FIGS. 11A to 11D with time (hour) and a ratio (%) of the composition. Since the ubiquinol (b) is increasing with passing time within two hours, it was proved that the ubiquinone (a) was reduced by the skin tissue reducing apparatus 1. The ubiquinone and vitamin K are the same group and the ubiquinone is converted into the ubiquinole in a live body of the human or the like. The ubiquinone is an activated substance having a strong reducing effect and an anti-oxidation operation and is effective for the human body. That is, it is possible to convert the vitamin K into the activated substance and the activated substance becomes to the ubiquinone after the operation due to the ubiquinol. Then, the skin tissue reducing apparatus 1 can again convert the ubiquinone into the activated substance. Therefore, the skin tissue reducing apparatus 1 of the present invention is also able to activate the vitamin K.

Figure 13A:
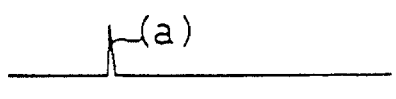
FIGS. 13A and 13B are graphs showing an HPLC of the ubiquinone in E$_t$OH solutions before and after irradiation of the skin tissue reducing apparatus according to the present invention.
Figure 13B:
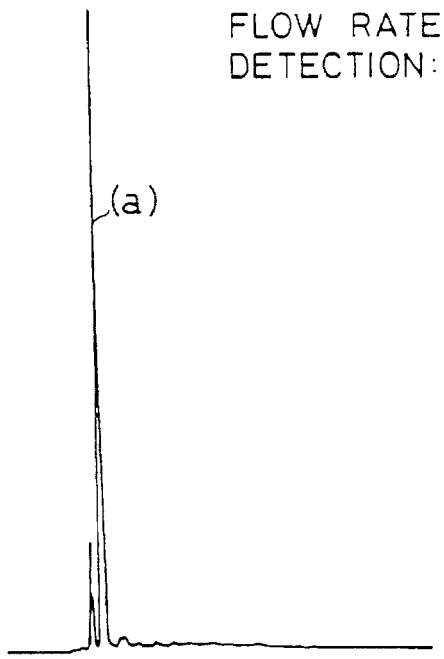

FIGS. 13A and 13B show the high performance liquid chromatogram of an ubiquinone in EtOH:Ether solution (3:1), in which the contact element 30 of the present invention was immersed and worked. The analysis result shown in FIG. 13A at start time shows that the solution has 100% of the ubiquinone (a) o The analysis result shown in FIG. 13B after two hours shows similarly that the solution has 100% of the ubiquinone (a). This means that the ubiquinol is not formed by reducing the ubiquinone in a non-aqueous system.

As stated above, since the reduction from the ubiquinone to the ubiquinol is not formed in non-aqueous solvent, but is formed in aqueous solvent, the reduction of organic compounds by the skin tissue reducing apparatus 1 need water ($H_2O$). Namely, it is considered that protons require reduction of carbonyl groups given by the water.

Although the contact element 30 is made of a glass tube as shown in FIGS. 1 and 2, it may be made of a metal plate 34 of which the surface is coated fluororesin layer 35 as shown in FIGS. 14A and 14B.

As stated by the above explanations, according to the method and the apparatus of the present invention, the oxidized skin tissue can be reduced in a short time and deterioration of the skin can be prevented since the negative electrons are added to the oxidized skin tissue. In addition, by measuring the reduction power of a pyrogallol solution containing a predetermined amount of vitamin C, the correlation between the amount of vitamin C and the working time of the present invention can be obtained. The effect equivalent to, or more than, that provided by ingestion of the vitamin C of the predetermined amount can be efficiently achieved by the present invention.

It should be understood that many modifications and adaptations of the invention will become apparent to those skilled in the art and it is intended to encompass such obvious modifications and changes in the scope of the claims appended hereto.

What is claimed is:

1. A method for reducing oxidized skin tissue, comprising the steps of:

providing a contact element which is connected to a high-voltage pulse generating means for generating negative high-voltage pulses;

generating negative high-voltage pulses by the high-voltage pulse generating means;

adjusting a duty ratio and a negative voltage of the negative high-voltage pulses to a pertinent ratio and a predetermined voltage, respectively;

supplying said adjusted negative high-voltage pulses into the contact element, thereby generating electrons having negative charge in the contact element; and applying the electrons to a surface of an oxidized skin tissue through a contact portion of the contact element to reduce the oxidized skin tissue.

2. A method for reducing oxidized skin tissue according to claim 1, wherein said pertinent ratio is 1/1999 and said predetermined voltage is −15 kV.

3. An apparatus for reducing skin tissue, comprising:

a high-voltage pulse generating means for generating negative high-voltage pulses of which duty ratio and voltage are respectively adjustable; and a contact element having an electrode connected to the high-voltage pulse generating means and a contact portion, said contact element providing means for applying electrons due to negative high-voltage pulses from said contact portion to a surface of an oxidized skin tissue, whereby the oxidized skin tissue is reduced by an electron addition reaction.

4. An apparatus for reducing skin tissue according to claim 3, wherein the high voltage pulse generating means comprises a pulse generating portion that outputs pulses of which duty ratio and pulse voltage are respectively adjustable, and an outputting portion having a voltage step-up transformer that steps-up and outputs the negative high-voltage pulses.

5. An apparatus for reducing skin tissue according to claim 4, wherein the pulse generating portion includes an electronic switching means which is in series connected with a primary coil of the voltage step-up transformer, a main capacitor which is in parallel connected with the primary coil of the voltage step-up transformer, and a charging circuit for charging the main capacitor.

6. An apparatus for reducing skin tissue according to claim 5, wherein the pulse generating portion further includes a trigger pulse generating circuit which provides a trigger pulse for controlling the electronic switching means, and a voltage detecting circuit for detecting a voltage of the main capacitor and controlling the charging circuit and the trigger pulse generating circuit.

7. An apparatus for reducing skin tissue according to claim 6, wherein the outputting portion includes a bleeder resistor which is in parallel connected with a secondary coil of the voltage step-up transformer.

8. An apparatus for reducing skin tissue according to claim 7, wherein the contact element comprises a glass tube with the electrode coated on one end, and depressurized air or gas is sealed in the glass tube.

9. An apparatus for reducing skin tissue according to claim 7, wherein the primary coil and the secondary coil are resonance type inductive coils.

10. An apparatus for reducing skin tissue according to claim 7, wherein the primary coil and the secondary coil are non-resonance type inductive coils.

11. An apparatus for reducing skin tissue according to claim 3, wherein the contact element comprises a glass tube in which gas and the electrode are sealed inside the glass tube.

12. An apparatus for reducing skin tissue according to claim 4, wherein the contact element comprises a glass tube in which gas is sealed inside and a metal deposition electrode is formed on the inner wall of the glass tube.

13. An apparatus for reducing skin tissue according to claim 4, wherein the contact element comprises a metal plate which is coated with an insulating material.

14. An apparatus for reducing skin tissue according to claim 4, wherein the contact element comprises a foil which is coated with an insulating material.

15. An apparatus for reducing skin tissue according to claim 4, wherein the contact element comprises a net which is coated with an insulating material.

* * * * *